United States Patent
Pirio et al.

(10) Patent No.: US 10,276,021 B2
(45) Date of Patent: Apr. 30, 2019

(54) PATIENT SUPPORT APPARATUS HAVING ARTICULATED MATTRESS SUPPORT DECK WITH LOAD SENSORS

(71) Applicant: Hill-Rom SAS, Pluvigner (FR)

(72) Inventors: Clementine Pirio, Nantes (FR); Jean-Bernard Duvert, Auray (FR); Jean-Francois Tarsaud, Nimes (FR); Phillippe Kaikenger, Pluvigner (FR)

(73) Assignee: Hill-Rom SAS, Pluvigner (FR)

( * ) Notice: Subject to any disclaimer, the term of this patent is extended or adjusted under 35 U.S.C. 154(b) by 0 days.

(21) Appl. No.: 15/846,274

(22) Filed: Dec. 19, 2017

(65) Prior Publication Data

US 2018/0108239 A1    Apr. 19, 2018

Related U.S. Application Data

(63) Continuation of application No. 14/847,164, filed on Sep. 8, 2015, now Pat. No. 9,875,633.

(30) Foreign Application Priority Data

Sep. 11, 2014    (EP) ..................................... 14306400

(51) Int. Cl.
*G08B 21/04*    (2006.01)
*A61G 7/005*    (2006.01)
(Continued)

(52) U.S. Cl.
CPC ........ *G08B 21/0461* (2013.01); *A61B 5/1115* (2013.01); *A61B 5/6892* (2013.01);
(Continued)

(58) Field of Classification Search
CPC ................ A61B 5/6892; A61B 5/1115; A61B 2562/0247; A61B 2562/0252;
(Continued)

(56) References Cited

U.S. PATENT DOCUMENTS

| 1,969,554 A | 8/1934 | Gloudemans |
| 2,735,291 A | 2/1956 | Quinn |

(Continued)

FOREIGN PATENT DOCUMENTS

WO    WO 2012/122002    *    9/2013

*Primary Examiner* — Hongmin Fan
(74) *Attorney, Agent, or Firm* — Barnes & Thornburg LLP

(57) ABSTRACT

A patient support apparatus comprises a substantially rigid support deck for supporting a patient support element, a first sensing element and a second sensing element arranged on the support deck and separated from one another in a direction along the width of the patient support apparatus. Each sensing element is configured to determine, in use, the force or pressure applied to it by the patient support element and a patient on the patient support element. One or more processors, coupled to the sensing elements, are configured to determine the location of the center of gravity of a patient on the patient support element, along the width of the patient support apparatus, based upon outputs of the first and second sensing elements. An alarm may be activated when the location of the center of gravity along the width of the patient support apparatus is outside a predetermined range of values.

20 Claims, 10 Drawing Sheets

(51) Int. Cl.
G08B 21/22 (2006.01)
A61B 5/00 (2006.01)
A61B 5/11 (2006.01)

(52) U.S. Cl.
CPC .............. *A61G 7/005* (2013.01); *G08B 21/22* (2013.01); *A61B 2562/0247* (2013.01); *A61B 2562/0252* (2013.01); *A61G 2203/32* (2013.01)

(58) Field of Classification Search
CPC .... G08B 21/0461; G08B 21/22; A61G 7/005; A61G 2203/32
See application file for complete search history.

(56) References Cited

U.S. PATENT DOCUMENTS

| | | |
|---|---|---|
| 2,784,395 A | 3/1957 | Gorby |
| 2,990,899 A | 7/1961 | De Bella |
| 3,096,061 A | 7/1963 | Bertell |
| 3,217,818 A | 11/1965 | Engelsher et al. |
| 3,338,323 A | 8/1967 | Swersey |
| 3,360,062 A | 12/1967 | Potter |
| 3,512,595 A | 5/1970 | Laimins |
| 3,589,457 A | 6/1971 | Joos |
| 3,656,478 A | 4/1972 | Swersey |
| 3,722,611 A | 3/1973 | Tirkkonen |
| 3,741,328 A | 6/1973 | Andersson et al. |
| 3,766,344 A | 10/1973 | Nevett |
| 3,773,124 A | 11/1973 | Bullivant |
| 3,795,284 A | 3/1974 | Mracek et al. |
| 3,796,208 A | 3/1974 | Bloice |
| 3,852,736 A | 12/1974 | Cook et al. |
| 3,876,018 A | 4/1975 | Mracek et al. |
| 3,890,958 A | 6/1975 | Fister et al. |
| 3,961,201 A | 6/1976 | Rosenthal |
| 3,961,627 A | 6/1976 | Ernst et al. |
| 3,961,675 A | 6/1976 | Siegel |
| 3,972,320 A | 8/1976 | Kalman |
| 3,991,414 A | 11/1976 | Moran |
| 3,991,415 A | 11/1976 | Baar |
| 3,991,746 A | 11/1976 | Hanna |
| 4,006,789 A | 2/1977 | Stultz et al. |
| 4,015,677 A | 4/1977 | Silva et al. |
| 4,020,482 A | 4/1977 | Feldl |
| 4,023,633 A | 5/1977 | Swersey et al. |
| 4,033,420 A | 7/1977 | De Masters |
| 4,067,005 A | 1/1978 | Levy et al. |
| 4,129,189 A | 12/1978 | Maglecic et al. |
| 4,140,998 A | 2/1979 | Bettle |
| 4,150,326 A | 4/1979 | Engelberger et al. |
| 4,175,263 A | 11/1979 | Morrow et al. |
| 4,179,692 A | 12/1979 | Vance |
| 4,180,803 A | 12/1979 | Haubner et al. |
| 4,188,621 A | 2/1980 | Heckelman et al. |
| 4,195,287 A | 3/1980 | Mathis et al. |
| 4,196,425 A | 4/1980 | Weekly et al. |
| 4,199,792 A | 4/1980 | Satoh et al. |
| 4,228,426 A | 10/1980 | Roberts |
| 4,242,672 A | 12/1980 | Gault |
| 4,245,651 A | 1/1981 | Frost |
| 4,257,035 A | 3/1981 | Yen |
| 4,281,730 A | 8/1981 | Swersey et al. |
| 4,282,412 A | 8/1981 | Florin |
| 4,290,136 A | 9/1981 | Brunner et al. |
| 4,295,133 A | 10/1981 | Vance |
| 4,320,766 A | 3/1982 | Alihanka et al. |
| 4,323,064 A | 4/1982 | Hoenig et al. |
| 4,335,468 A | 6/1982 | Foster et al. |
| 4,336,533 A | 6/1982 | Wettach |
| 4,346,771 A | 8/1982 | Persson et al. |
| 4,350,860 A | 9/1982 | Ueda |
| 4,363,368 A | 12/1982 | Paddon et al. |
| 4,419,830 A | 12/1983 | Miller |
| 4,420,052 A | 12/1983 | Hale |
| 4,426,644 A | 1/1984 | Neumann et al. |
| 4,438,823 A | 3/1984 | Hussels et al. |
| 4,475,013 A | 10/1984 | Lee et al. |
| 4,482,783 A | 11/1984 | Laimins |
| 4,483,404 A | 11/1984 | Weihs |
| 4,484,043 A | 11/1984 | Musick et al. |
| 4,492,281 A | 1/1985 | Van Allen et al. |
| 4,519,027 A | 5/1985 | Vogelsberg |
| 4,539,560 A | 9/1985 | Fleck et al. |
| 4,540,057 A | 9/1985 | Freeman |
| 4,550,793 A | 11/1985 | Giles |
| 4,551,029 A | 11/1985 | Aizawa |
| 4,551,882 A | 11/1985 | Swersey et al. |
| 4,558,181 A | 12/1985 | Blanchard et al. |
| 4,572,006 A | 2/1986 | Wolfendale |
| 4,577,709 A | 3/1986 | Shibahara et al. |
| 4,583,084 A | 4/1986 | Henderson et al. |
| 4,587,739 A | 5/1986 | Holcomb et al. |
| 4,597,487 A | 7/1986 | Crosby et al. |
| 4,600,066 A | 7/1986 | Griffen et al. |
| 4,601,356 A | 7/1986 | Muccillo |
| 4,629,015 A | 12/1986 | Fried et al. |
| 4,633,237 A | 12/1986 | Tucknott et al. |
| 4,638,307 A | 1/1987 | Swartout |
| 4,638,876 A | 1/1987 | Balduin et al. |
| 4,649,759 A | 3/1987 | Lee |
| 4,659,233 A | 4/1987 | Nakamura et al. |
| 4,670,864 A | 6/1987 | Hoffmann |
| 4,679,144 A | 7/1987 | Cox et al. |
| 4,696,358 A | 9/1987 | Doerman et al. |
| 4,738,325 A | 4/1988 | Bullivant |
| 4,751,754 A | 6/1988 | Bailey et al. |
| 4,757,867 A | 7/1988 | Rosenthal et al. |
| 4,793,428 A | 12/1988 | Swersey |
| 4,796,013 A | 1/1989 | Yasuda et al. |
| 4,805,637 A | 2/1989 | Walthert |
| 4,807,558 A | 2/1989 | Swersey |
| 4,845,323 A | 7/1989 | Beggs |
| 4,858,622 A | 8/1989 | Osterweil |
| 4,865,581 A | 9/1989 | Lundquist et al. |
| 4,866,356 A | 9/1989 | Altendorf |
| 4,899,840 A | 2/1990 | Boubille |
| 4,907,845 A | 3/1990 | Wood |
| 4,934,468 A | 6/1990 | Koerber et al. |
| 4,947,298 A | 8/1990 | Stephen |
| 4,953,244 A | 9/1990 | Koerber et al. |
| 4,953,277 A | 9/1990 | Crispin et al. |
| 4,961,470 A | 10/1990 | Koerber, Sr. |
| 4,967,384 A | 10/1990 | Molinar et al. |
| 4,974,692 A | 12/1990 | Carruth et al. |
| 5,007,420 A | 4/1991 | Bird |
| 5,019,905 A | 5/1991 | Pshtissky et al. |
| 5,033,563 A | 7/1991 | Brainerd et al. |
| 5,140,309 A | 8/1992 | Gusakov |
| 5,166,679 A | 11/1992 | Vranish et al. |
| 5,183,126 A | 2/1993 | Kellenbach |
| 5,184,112 A | 2/1993 | Gusakov |
| 5,184,122 A | 2/1993 | Decious et al. |
| 5,224,561 A | 7/1993 | Afl |
| 5,232,064 A | 8/1993 | Kroll et al. |
| 5,235,319 A | 8/1993 | Hill et al. |
| 5,269,388 A | 12/1993 | Reichow et al. |
| 5,276,432 A | 1/1994 | Travis |
| 5,353,012 A | 10/1994 | Barham et al. |
| 5,393,935 A | 2/1995 | Hasty et al. |
| 5,393,938 A | 2/1995 | Bumbalough |
| 5,410,297 A | 4/1995 | Joseph et al. |
| 5,446,391 A | 8/1995 | Aoki et al. |
| 5,448,996 A | 9/1995 | Bellin et al. |
| 5,471,198 A | 11/1995 | Newham |
| 5,479,939 A | 1/1996 | Ogino |
| 5,519,380 A | 5/1996 | Edwards |
| RE35,301 E | 7/1996 | Reichow |
| 5,554,835 A | 9/1996 | Newham |
| 5,600,104 A | 2/1997 | McCauley et al. |
| 5,600,305 A | 2/1997 | Stafford et al. |
| 5,606,516 A | 2/1997 | Douglas et al. |
| 5,623,760 A | 4/1997 | Newham |
| 5,633,627 A | 5/1997 | Newham |
| 5,640,145 A | 6/1997 | Newham |

(56) References Cited

U.S. PATENT DOCUMENTS

| | | |
|---|---|---|
| 5,654,694 A | 8/1997 | Newham |
| 5,672,849 A | 9/1997 | Foster et al. |
| 5,700,982 A | 12/1997 | Neuman |
| 5,723,826 A | 3/1998 | Kitagawa et al. |
| 5,747,745 A | 5/1998 | Neuman |
| 5,760,688 A | 6/1998 | Kasai |
| 5,767,774 A | 6/1998 | Wright et al. |
| 5,780,781 A * | 7/1998 | Berger ............. G01G 19/445 177/126 |
| 5,796,059 A | 8/1998 | Boon |
| 5,798,487 A | 8/1998 | Goichman et al. |
| 5,801,339 A | 9/1998 | Boult |
| 5,808,552 A | 9/1998 | Wiley et al. |
| 5,823,278 A | 10/1998 | Geringer |
| 5,827,981 A | 10/1998 | March |
| 5,831,221 A | 11/1998 | Geringer et al. |
| 5,844,488 A | 12/1998 | Musick |
| 5,859,390 A | 1/1999 | Stafford et al. |
| 5,861,581 A | 1/1999 | Evans et al. |
| 5,861,582 A | 1/1999 | Flanagan et al. |
| 5,864,295 A | 1/1999 | Jarocha |
| 5,869,788 A | 2/1999 | Gordon et al. |
| 5,879,309 A | 3/1999 | Johnson et al. |
| 5,880,410 A | 3/1999 | Neuman |
| 5,896,090 A | 4/1999 | Okada et al. |
| 5,906,016 A | 5/1999 | Ferrand et al. |
| 5,910,647 A | 6/1999 | Kats et al. |
| 5,941,836 A | 8/1999 | Friedman |
| 5,957,838 A | 9/1999 | Rantala |
| 5,990,423 A | 11/1999 | Ashpes et al. |
| 5,991,676 A | 11/1999 | Podoloff et al. |
| 6,020,812 A | 2/2000 | Thompson et al. |
| 6,033,370 A | 3/2000 | Reinbold et al. |
| 6,036,660 A | 3/2000 | Toms |
| 6,040,532 A | 3/2000 | Munch |
| 6,049,281 A | 4/2000 | Osterweil |
| D424,650 S | 5/2000 | Reichow |
| 6,056,079 A | 5/2000 | Cech et al. |
| 6,067,019 A | 5/2000 | Scott |
| 6,075,464 A | 6/2000 | Cloutier et al. |
| 6,078,253 A | 6/2000 | Fowler |
| 6,078,261 A | 6/2000 | Davsko |
| 6,080,106 A | 6/2000 | Lloyd et al. |
| 6,092,838 A | 7/2000 | Walker |
| 6,133,743 A | 10/2000 | Gleixner et al. |
| 6,133,837 A | 10/2000 | Riley |
| 6,166,644 A | 12/2000 | Stroda |
| D436,322 S | 1/2001 | Wajer |
| 6,180,893 B1 | 1/2001 | Salgo |
| 6,204,767 B1 | 3/2001 | Sparks |
| 6,208,249 B1 | 3/2001 | Saito |
| 6,208,250 B1 | 3/2001 | Dixon et al. |
| 6,239,706 B1 | 5/2001 | Yoshiike et al. |
| 6,250,671 B1 | 6/2001 | Osmer et al. |
| 6,297,738 B1 | 10/2001 | Newham |
| 6,307,476 B1 | 10/2001 | Smith et al. |
| 6,320,510 B2 | 11/2001 | Menkedick et al. |
| 6,348,663 B1 | 2/2002 | Schoos et al. |
| 6,362,439 B1 | 3/2002 | Reichow |
| 6,367,314 B1 | 4/2002 | Melton |
| 6,438,776 B2 | 8/2002 | Ferrand et al. |
| 6,518,520 B2 | 2/2003 | Jones et al. |
| 6,546,813 B2 | 4/2003 | Hubbard |
| 6,636,820 B2 | 10/2003 | Livingston |
| 6,668,408 B2 | 12/2003 | Ferrand et al. |
| 6,680,443 B2 | 1/2004 | Dixon |
| 6,719,708 B1 | 4/2004 | Jansen |
| 6,784,797 B2 | 8/2004 | Smith et al. |
| 6,791,460 B2 | 9/2004 | Dixon et al. |
| 6,822,571 B2 | 11/2004 | Conway |
| 6,829,796 B2 | 12/2004 | Salvatini et al. |
| 6,840,117 B2 | 1/2005 | Hubbard, Jr. |
| 6,843,109 B2 | 1/2005 | Nakada et al. |
| 6,847,301 B1 | 1/2005 | Olson |
| 6,924,441 B1 | 8/2005 | Mobley et al. |
| 6,941,598 B2 | 9/2005 | Ferrand et al. |
| 6,969,809 B2 | 11/2005 | Rainey |
| 7,009,509 B2 | 3/2006 | Sakai |
| 7,100,439 B2 | 9/2006 | Carlucci |
| 7,126,065 B2 | 10/2006 | Petrucelli |
| 7,176,391 B2 | 2/2007 | Metz et al. |
| 7,202,424 B2 | 4/2007 | Carlucci |
| 7,253,366 B2 | 8/2007 | Bhai |
| 7,292,150 B2 | 11/2007 | Shaw |
| 7,310,839 B2 | 12/2007 | Salvatini et al. |
| 7,335,839 B2 | 2/2008 | Metz et al. |
| 7,437,787 B2 | 10/2008 | Bhai |
| 7,469,436 B2 | 12/2008 | Meyer et al. |
| 7,500,280 B2 | 3/2009 | Dixon et al. |
| 7,557,718 B2 | 7/2009 | Petrosenko et al. |
| 7,568,246 B2 | 8/2009 | Weismiller et al. |
| 7,578,416 B2 | 8/2009 | Underwood |
| 7,656,299 B2 | 2/2010 | Gentry et al. |
| 7,666,151 B2 | 2/2010 | Sullivan et al. |
| 7,698,765 B2 | 4/2010 | Bobey et al. |
| 7,699,784 B2 | 4/2010 | Wan Fong et al. |
| 7,714,238 B2 | 5/2010 | Skinner et al. |
| 7,761,310 B2 | 7/2010 | Rodgers |
| 7,786,874 B2 | 8/2010 | Rodgers |
| 7,790,022 B2 | 9/2010 | Underwood et al. |
| 7,834,768 B2 | 11/2010 | Dixon et al. |
| 7,834,770 B2 | 11/2010 | Kazuno |
| 7,849,545 B2 | 12/2010 | Flocard et al. |
| 7,897,884 B2 | 3/2011 | Harish |
| 7,911,348 B2 | 3/2011 | Rodgers |
| 7,924,163 B1 | 4/2011 | Long et al. |
| 7,937,791 B2 | 5/2011 | Meyer et al. |
| 7,973,666 B2 | 7/2011 | Petrosenko et al. |
| 7,978,084 B2 | 7/2011 | Dixon et al. |
| 7,986,242 B2 | 7/2011 | Dixon et al. |
| 7,987,069 B2 | 7/2011 | Rodgers et al. |
| 8,048,005 B2 | 11/2011 | Dixon et al. |
| 8,090,478 B2 | 1/2012 | Skinner et al. |
| 8,146,191 B2 | 4/2012 | Bobey et al. |
| 8,161,826 B1 | 4/2012 | Taylor |
| 8,196,240 B2 | 6/2012 | Meyer et al. |
| 8,258,963 B2 | 9/2012 | Dixon et al. |
| 8,272,087 B2 | 9/2012 | Westermann |
| 8,302,227 B2 | 11/2012 | Jensen |
| 8,344,860 B2 | 1/2013 | Collins, Jr. et al. |
| 8,376,964 B2 | 2/2013 | Park et al. |
| 8,381,336 B2 | 2/2013 | Kazuno et al. |
| 8,400,311 B2 | 3/2013 | Dixon et al. |
| 8,403,864 B2 | 3/2013 | Boecker et al. |
| 8,419,660 B1 | 4/2013 | Shaw |
| 8,432,287 B2 | 4/2013 | O'Keefe et al. |
| 8,464,380 B2 | 6/2013 | Bobey et al. |
| 8,491,492 B2 | 7/2013 | Shinar et al. |
| 8,517,953 B2 | 8/2013 | Lange et al. |
| 8,525,680 B2 | 9/2013 | Riley et al. |
| 8,525,682 B2 | 9/2013 | Dixon et al. |
| 8,533,879 B1 | 9/2013 | Taylor |
| 8,537,008 B2 | 9/2013 | Tallent et al. |
| 8,585,607 B2 | 11/2013 | Klap et al. |
| 8,593,284 B2 | 11/2013 | Tallent et al. |
| 8,598,893 B2 | 12/2013 | Camus |
| 8,603,010 B2 | 12/2013 | Lange et al. |
| 8,783,114 B2 | 7/2014 | Anderson et al. |
| 9,875,633 B2 | 1/2018 | Pirio et al. |
| 2001/0015292 A1 | 8/2001 | Salgo |
| 2001/0020395 A1 | 9/2001 | Hubbard, Jr. |
| 2002/0070867 A1 | 6/2002 | Conway et al. |
| 2002/0080037 A1 | 6/2002 | Dixon et al. |
| 2003/0090383 A1 | 5/2003 | Conway |
| 2003/0136201 A1 | 7/2003 | Hubbard, Jr. |
| 2004/0046668 A1 | 3/2004 | Smith et al. |
| 2004/0111045 A1 | 6/2004 | Sullivan et al. |
| 2006/0028350 A1 * | 2/2006 | Bhai ............... A61B 5/1115 340/666 |
| 2006/0070456 A1 | 4/2006 | Douglas et al. |
| 2006/0152358 A1 | 7/2006 | Osterweil |
| 2006/0277683 A1 | 12/2006 | Lamire et al. |
| 2006/0279426 A1 | 12/2006 | Bonnet et al. |
| 2006/0293613 A1 | 12/2006 | Fatehi et al. |

(56) References Cited

U.S. PATENT DOCUMENTS

| | | |
|---|---|---|
| 2007/0268147 A1 | 11/2007 | Bhai |
| 2007/0272450 A1 | 11/2007 | Skinner et al. |
| 2008/0132808 A1 | 6/2008 | Lokhorst et al. |
| 2008/0169931 A1 | 7/2008 | Gentry et al. |
| 2008/0204254 A1* | 8/2008 | Kazuno .............. G08B 21/0461 340/573.4 |
| 2009/0151081 A1 | 6/2009 | Wu et al. |
| 2009/0260158 A1 | 10/2009 | Kazuno et al. |
| 2010/0299840 A1 | 12/2010 | Brauers et al. |
| 2011/0234408 A1 | 9/2011 | Dixon et al. |
| 2012/0011941 A1 | 1/2012 | Anderson et al. |
| 2013/0174345 A1 | 7/2013 | Leu et al. |
| 2014/0039351 A1 | 2/2014 | Mix et al. |
| 2014/0068860 A1 | 3/2014 | Shih |
| 2014/0135659 A1* | 5/2014 | Maggi ................... A61B 5/1116 600/595 |
| 2014/0266733 A1 | 9/2014 | Hayes et al. |
| 2014/0326072 A1 | 11/2014 | Anderson et al. |
| 2015/0351982 A1 | 12/2015 | Krenik |
| 2016/0078740 A1 | 3/2016 | Pirio et al. |
| 2016/0106345 A1 | 4/2016 | Kostic et al. |
| 2016/0161623 A1 | 6/2016 | Chacon et al. |

* cited by examiner

PATIENT SUPPORT APPARATUS HAVING ARTICULATED MATTRESS SUPPORT DECK WITH LOAD SENSORS

The present application is a continuation of U.S. application Ser. No. 14/847,164, filed Sep. 8, 2015, now U.S. Pat. No. 9,875,633, which claims priority, under 35 U.S.C. § 119(a), of European Application No. 14306400.4 which was filed Sep. 11, 2014 and each of which is hereby incorporated by reference herein.

BACKGROUND

The present disclosure is concerned with patient support apparatus and particularly with a patient detection system for detecting the presence of a patient on a patient-carrying surface of the patient support apparatus. Embodiments disclosed herein relate to apparatus for determining the force or pressure applied to the support deck by a patient on the patient support apparatus and means to thereby determine a location for the center of gravity of a patient on the patient support apparatus.

It is sometimes desirable to monitor the whereabouts of a patient, particularly when a doctor or other care giver has ordered that the patient remain on a patient-support device such as a hospital bed, a stretcher, or other device for carrying the patient. Several devices have been developed for detecting a patient exit from a patient-support device. For example, U.S. Pat. No. 5,276,432 to Travis discloses a bed exit detection mechanism for a hospital bed that relies on signals from load cells under the mattress supporting portion on the upper frame of the bed. The load cells support the upper bed frame and also any loads which are in turn supported by the frame, including a patient. This device uses the weight measured by each load cell to determine whether the center of gravity of the patient is over a predetermined region of the patient-carrying surface of the hospital bed. In addition, U.S. Pat. Nos. 4,934,468 and 4,953,244, disclose a hospital bed having a support frame and a weigh frame mounted on the support frame by load cells.

Arrangements such as that of U.S. Pat. No. 5,276,432 comprising a weigh frame or scales under the upper bed frame require expensive components and are therefore expensive. They are also difficult to retrofit to existing beds.

It is also known to monitor the position of a person by attaching a portion of a transmitter/receiver system to the person being monitored so that when the person and thus the portion of the system attached to the person leaves a designated area, the remaining portion of the system detects the departure of the portion and thus the departure of the person and provides an indication of the person's departure. For example, U.S. Pat. No. 5,519,380 to Edwards discloses a bracelet module that is worn by the monitored person so that when the person and the bracelet module move outside of the monitored volume, an indication of departure is provided.

It is also known to monitor the position of a patient on a bed using bladders or other fluid-carrying devices positioned to lie between the patient and the top of the mattress or other patient support surface of the bed. Such bladders or fluid-carrying devices are in fluid communication with a pressure sensor so that the pressure sensor registers a bladder pressure in response to the patient's weight, the bladder pressure indicating the presence or absence of the patient on the bladder. For example, U.S. Pat. Nos. 5,140,309 and 5,184,122, both to Gusakov, each disclose an apparatus including resilient means in the form of a tube, cell or other form of fluid passage adapted to allow fluid such as air to flow from an inlet through the outlet when a passage is not collapsed by the weight of a patient. Indicating means indicate changes in pressure in the fluid supplied by the fluid supplying means, such as when the weight of a patient collapses the passage through the resilient means. By providing resilient means having a plurality of tubes, cells or other fluid passages and separate indicating means for each resilient means, the position of the patient relative to each resilient means can be monitored.

There are also several known systems that include sensors positioned to lie immediately beneath the patient (between the patient and the mattress or other patient support surface) and that provide electrical signals in response to the weight detected by the sensor so that an output signal indicating a significant change of weight acting against the sensor indicates movement of the patient to a position away from the sensor or to a position on top of the sensor. For example, U.S. Pat. No. 5,353,012 to Barham et al.; Swartout disclose a system which includes a sensor that provides an output signal in response to a change in the weight acting against the sensor.

Finally, it is also known to provide capacitive motion sensors for monitoring the movements of a person and even for measuring respiration, heartbeat, and body position of the person. For example, U.S. Pat. No. 4,320,766 to Alihanka et al. and U.S. Pat. No. 5,448,996 to Bellin et al. each disclose patient monitors including capacitive sensors. The device disclosed by the Alihanka patent can indicate that movement has occurred but cannot indicate what movement occurred or the position of the body when no movement is occurring, and the Bellin patent likewise can indicate movement but not position of the patient or that a patient has exited the bed.

Improvements in bed mattress designs have significantly reduced peak interface pressure between the patient and the mattress by maximizing the area over which the weight of the patient is distributed rather than concentrating the interface pressure at points along the patient, for example, the patient's head, shoulder blades and heels. In addition, recent patient population data indicates that some patients in general weigh less than in the past. Patient detection systems that rely on the weight of the patient to allow the sensor to detect the patient are rendered less effective as mattresses become more efficient at distributing the weight of the patient across the surface of the mattress and as the weight of the patient decreases. In addition, while it is desirable to minimize the interface pressure of high interface pressure points between the patient and the mattress by distributing the weight of the patient across the mattress, for example, by using mattresses including air bladder supports, interposing a sensor between the top surface of the mattress and the patient significantly reduces the effectiveness of the mattress at distributing the weight of the patient. In addition, for applications in which it is desirable to keep the patient dry and maintain the temperature of the patient at a desired temperature through the use of a "low air loss" mattress that allows a very small amount of air to escape the mattress and blow on the patient, interposing a sensor between the patient and the mattress reduces the effectiveness of the low air loss feature.

What is needed is a sensor that can sense the position of a patient relative to a patient-carrying surface of a patient-support device that can be positioned to lie away from the patient allowing the sensor to be placed away from the patient-carrying surface. In addition, the sensor should not require the attachment of a portion of the system to the patient.

U.S. Pat. No. 6,067,019 to Scott discloses a bed exit detection apparatus including a number of bed position sensors arranged underneath the mattress between the mattress and the mattress support frame or surface. The sensors each comprise separated conducting plates which together form a capacitor having a capacitor gap whose dielectric consent is affected by the absence or presence of a portion of a human body arranged above, but separated by the mattress from the respective sensor.

The complicated dielectric/capacitive sensor arrangement of Scott was considered necessary in order to overcome the perceived difficulties associated with sensing for the absence or presence of a body remote from the sensors (i.e. separated therefrom by the mattress) and in which the presence of the mattress would distribute the weight of the patient and thereby create difficulties.

SUMMARY

The present application, in a first aspect, discloses a patient support apparatus comprising a substantially rigid support deck for supporting a patient support element, and at least one sensing element arranged on the support deck, wherein the or each sensing element determines the force or pressure applied to it by the patient support element and a patient on the patient support element, and the apparatus includes one or more processors coupled to the at least one sensing element for determining a location for the center of gravity of a patient on the patient support element from the sensing element outputs.

Optionally, the patient support apparatus comprises at least two sensing elements. Optionally, three or more sensing elements may be used. The sensing elements may be arranged such that the center of gravity of a combined patient and mattress will be, when the patient is in a normal safe position, located within an area bounded by the sensing element. The outputs from the sensing elements are, together, enough to determine the location of the center of gravity and thereby monitor the position of a patient.

The inventor of the subject application has appreciated that, contrary to the existing technical prejudice, it is possible to adequately and safely monitor a patient's position using the at least one sensing element arranged between a substantially rigid support deck and a patient support element for example a mattress. The elements necessary to implement such a system on a bed are relatively inexpensive and while such an arrangement might be less accurate than some of the known arrangements, it is sufficiently accurate and robust for inexpensive patient portion monitoring and detecting bed exit by a patient.

Optionally, the patient support element is a mattress.

Optionally, at least two of the at least three sensing elements are supported on a sensing pad or board. A sensing board can be easily made and then retro-fitted to existing beds or patient support apparatus.

Optionally, the apparatus includes two sensing boards or pads and wherein each sensing board or pad includes at least two sensing elements. This arrangement has enough sensors in different locations which allow for a sufficiently accurate determination from the loads measured at each sensing element of the location of the center of gravity of a mattress or patient support element (with or without a patient on its upper surface). Optionally, the sensing pad or board is a substantially rigid board and the sensing elements are attached to the underside of the board.

Optionally, one sensing board or pad is located on the support deck so that, in use, it is underneath the seat of a patient in a normal supine or lying down position on the patient support element, and a second sensing board or pad is located on the support deck so that, in use, it is underneath the thighs of a patient in a normal supine or lying down position on the patient support element. It is believed that the inventor of the subject application is the first to determine that such an arrangement allows for a sufficiently accurate determination of the location of the center of gravity without the need for significant numbers of sensors. This makes for a relatively inexpensive system for monitoring a patient on a patient support apparatus.

Optionally, the sensing board or pad is substantially rectangular and includes four sensing elements, each of the four sensing elements being at or near each of the four corners of the sensing board or pad. This is a robust and easy to make arrangement.

Optionally, the sensing elements are thin flexible sensing elements attached to or integral with the bottom surface of the mattress. Optionally the thin flexible sensing elements are integral with or attached to the lower surface of the mattress.

Optionally, the sensing elements are selected from the group comprising the following types of load cell sensing elements: strain gauge sensors, extensometers, bending beam sensors, hall-effect sensors and/or capacitive sensors.

Optionally, the sensing elements are capacitive sensors. Such sensors can be flexible and thin and therefore are suitable for integration with, or attachment to, a mattress or other patient support element.

The patient support apparatus, in a second aspect, comprises a substantially rigid support deck for supporting a patient support element and a first sensing element and a second sensing element separated from one another in a direction along the width of the patient support apparatus. Each sensing element is configured to determine, in use, the force or pressure applied to it by the patient support element and a patient on the patient support element. One or more processors are coupled to the sensing elements, the one or more processors being configured to determine or monitor the location for the center of gravity of a patient on the patient support element, along the width of the patient support apparatus between the sensors, based upon outputs of the first and second sensing elements; and to provide an output to activate an alarm when the location of the center of gravity along the width of the patient support apparatus is outside a predetermined range. This allows an alarm to be activated if a patient moves in a lateral direction, for example if they attempt to move towards the sides of the support apparatus, or they attempt to exit the bed.

Optionally, the one or more processors may be further configured to determine or monitor a load variation, being a variation in the total force applied to the sensing elements by the patient support element and a patient on the patient support element, and to provide an output to activate an alarm if the load variation exceeds a predetermined value. The monitoring of load variation allows further deductions to be made about the patient positioning.

Optionally, the one or more processors are configured to receive user input selecting one of two or more presets, each preset corresponding to a patient movement sensitivity level and comprising a predetermined range and/or predetermined load variation value stored on a memory; and to access the memory to receive the parameters associated with the selected preset. Different levels of sensitivity can therefore be provided depending upon the condition of the patient.

The patient support apparatus may optionally further comprise an adjustable back rest, and the one or more processors may be further configured to receive an input indicative of the angle of the back rest and to adjust the load variation or center of gravity by an amount dependent upon the angle of the back rest. The input may be provided by an accelerometer coupled to the back rest, the one or more processors being configured to receive an output from the accelerometer and to determine the angle of the back rest based on said output.

The patient support apparatus may optionally further comprise an adjustable back rest, and the one or more processors may be further configured to receive an input indicative of the angle of the back rest and to adjust the load variation by an amount dependent upon the change in angle of the back rest. The input may be provided by an accelerometer coupled to the back rest, the one or more processors being configured to receive an output from the accelerometer and to determine the angle of the back rest based on said output.

Optionally the one or more processors may be further configured to receive an input indicative of the type of patient support element and to adjust the location for the center of gravity based upon the input. For example, where the patient support element is a mattress the input may indicate whether the mattress is a foam mattress or an air mattress.

Optionally the patient support apparatus may further comprise a third sensing element and a fourth sensing element separated from one another in a direction along the width of the patient support apparatus, the third sensing element and the fourth sensing element being separated from the first sensing element and the second sensing element in a direction along the length of the patient support apparatus, the one or more processors being configured to determine the location for the center of gravity of a patient on the patient support element, along the width of the patient support apparatus, based upon outputs of the first, second, third and fourth sensing elements.

According to the second aspect a computer program may be provided which when executed on the one or more processors of the patient support apparatus described above or below causes it to carry out the methods described herein. In particular, the computer program may cause the patient support apparatus to determine the location for the center of gravity of a patient on the patient support element, along the width of the patient support apparatus, based upon outputs of the first and second sensing elements; and provide an output to activate an alarm when the location of the center of gravity along the width of the patient support apparatus is outside a predetermined range.

The present application, in a third aspect, provides a sensing board for use with a patient support apparatus to monitor the position of a patient on the patient support apparatus, the sensing board comprising a substantially rigid board for location on the patient support apparatus under a patient support element on the patient support apparatus and wherein the rigid board includes at least one sensing element that determines the force or pressure applied to it by the patient support element and a patient on the patient support element, and wherein the sensing board is coupled to data processing means for determining a location for the center of gravity of a patient on the patient support element from the sensing element outputs.

Such a sensing board can be easily retro-fitted to existing beds and provides a simple, robust and inexpensive system for patient position monitoring.

Optionally, the sensing board includes two or more sensing elements.

Optionally, the sensing elements are on the underside of the substantially rigid board.

Optionally, the sensing elements are selected from the group comprising the following types of load cell sensing elements: strain gauge sensors, extensometers, bending beam sensors, hall-effect sensors and/or capacitive sensors.

Optionally, the sensing board has at least two sensing elements and those two sensing elements are strain gauges.

The present application, in a fourth aspect, provides a system for sensing movement and/or inactivity of a patient on a patient support surface incorporating any embodiment of the apparatus described herein. Such a system can form part of a care protocol for reducing the risk of the bed sores and pressure ulcers associated with prolonged periods of patient inactivity.

Optionally, the system includes an arrangement configured to give a warning or alarm when the system detects a period of inactivity of a pre-defined length.

BRIEF DESCRIPTION OF THE DRAWINGS

Embodiments disclosed herein, in their various aspects, will now be described by way of non-limiting examples with reference to the accompanying drawings in which.

DETAILED DESCRIPTION

A patient detection system according to the present disclosure could be used to monitor the position of a patient relative to a patient-carrying surface of a bed as shown in the attached Figs. The system could also be used to determine position relative to the patient-carrying surfaces of other patient-support devices including chairs, wheelchairs, stretchers, operating tables, incubators, radiant warmers and other patient-support devices relative to which a caregiver may wish to monitor the presence or absence and the position of a patient.

Figure 1:
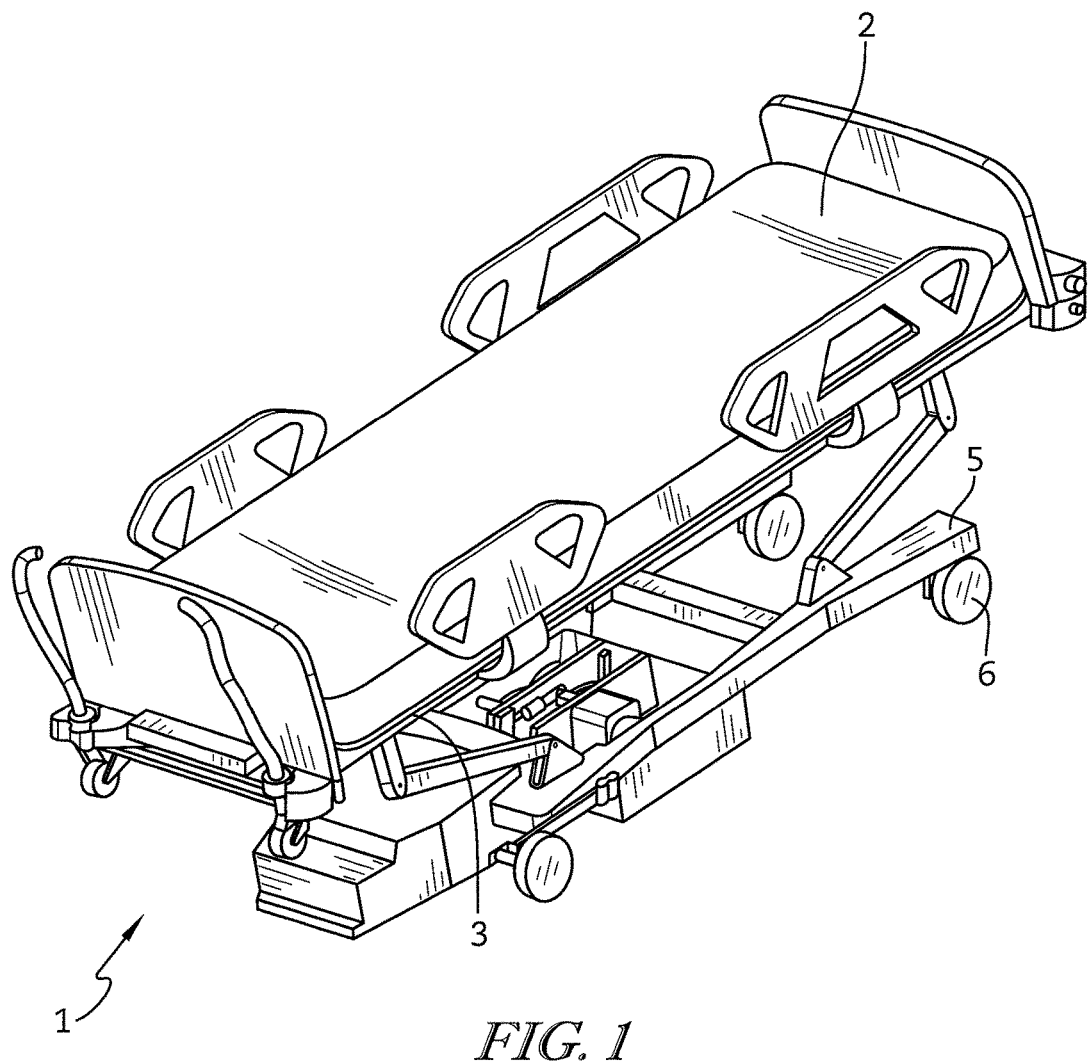
FIG. 1 is a perspective view of a hospital bed suitable for use with the various aspects of the subject application.

Referring to FIG. 1, a hospital or long-term care bed 1 includes a rigid support surface or deck 2 on an upper frame 3 which, in use, supports a mattress 4 or other patient-carrying element. The upper frame is supported on and moveable relative to a lower frame 5 which sits on casters 6. An upper frame support system 7 includes actuators which can move the upper frame and a mattress on that frame relative to the lower frame and hence relative to the floor. The bed and mattress are of known construction (see, for example, WO 2004/021952) so will not be described further. A sensing arrangement 8 is located between the mattress 4 and mattress support surface or deck 2.

The sensing arrangement 8 consists of a number of separate and independently operable load cells 9 which monitor the force or pressure exerted on their upper surface by the mattress 1 and a patient (not shown) on that mattress. The output from each load cell 9 is connected to patient position monitoring data processing hardware 10 and software 11 encompassed within a patient position monitoring unit 2.

Figure 2:
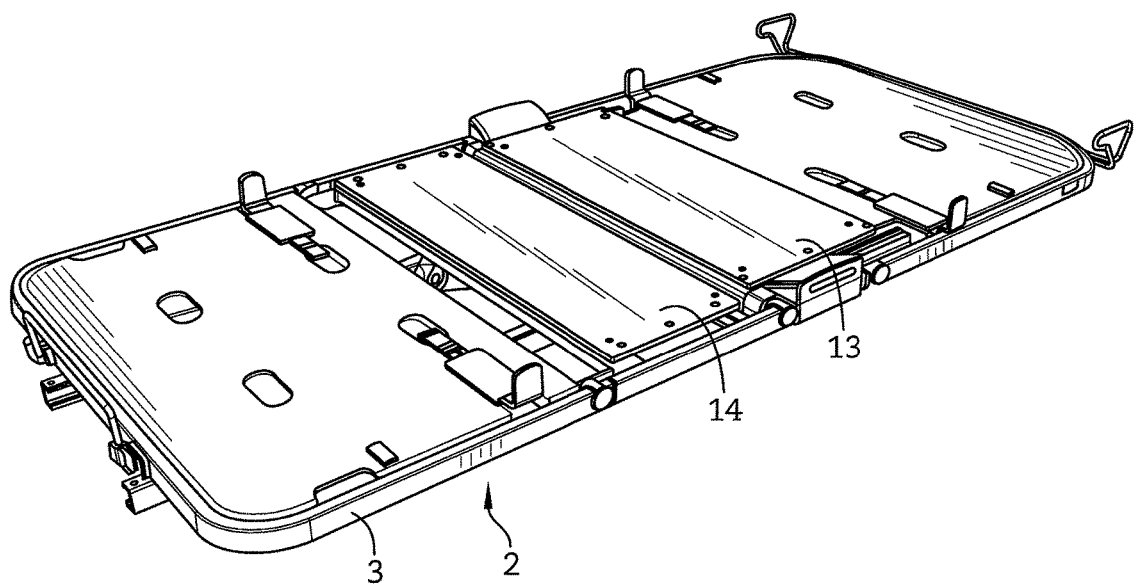
FIG. 2 is a top perspective view of the mattress support deck of the bed of FIG. 1.
Figure 3:
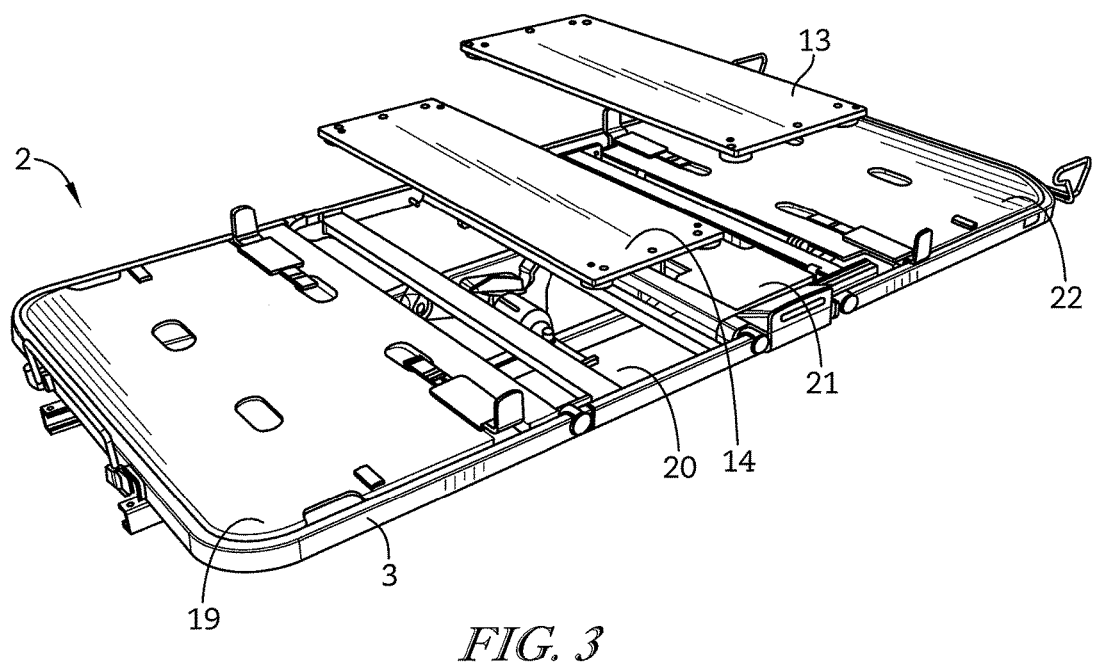
FIG. 3 is a top perspective view similar to FIG. 2 but with the sensing boards partially removed.
Figure 4:
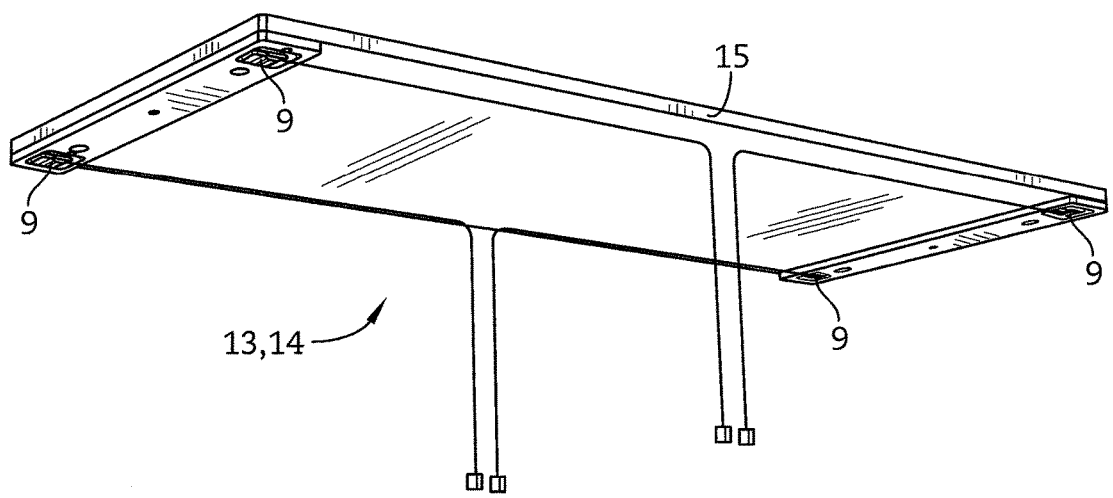
FIG. 4 is a bottom perspective schematic view of a sensing board of FIGS. 2 and 3.

Referring to FIGS. 2 and 3, two removable sensing boards 13, 14 are supported on the upper frame 3. One board 13 is positioned on the upper frame so that it is located under the seat of a patient supine on the bed in a normal position. The other board 14 is positioned so that it is located under the thighs of a patient supine on the bed in a normal position. They each comprise a rigid plastics panel 15 having four load cells 9 supported on the four corners of their underside. The load cells may be any sensor arrangement which senses the force or pressure applied to them. Such sensors include the following types of load cell sensing elements: strain gauge sensors, extensometers, bending beam sensors, hall-effect sensors and/or capacitive sensors. In the embodiment of FIGS. 2 to 4, the sensors or load cells 9 are each strain gauge sensors.

Figure 5:
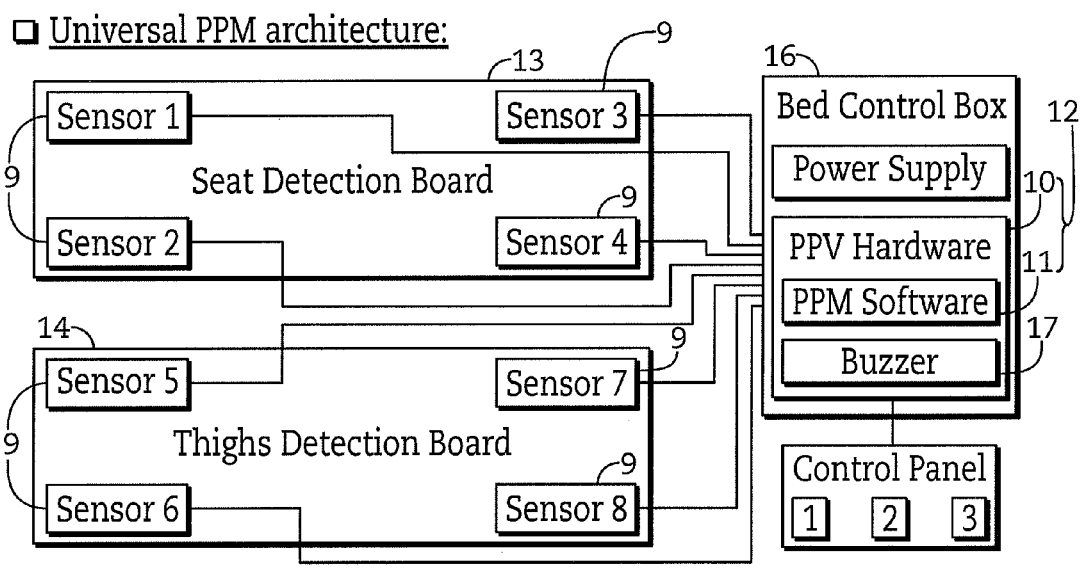
FIG. 5 is a top plan schematic view of a load cell and data processing arrangement for use with the arrangement of FIGS. 1 to 4.

Referring to FIGS. 4 and 5, the output from each sensing element is connected via wires to a bed control box 16 (not shown in FIG. 4). The bed control box includes data processing hardware 10 and software 11 which processes the forces sensed by each of the sensing elements 9 to determine the location of the center of gravity of the combined mattress and patient which weigh down on the sensing boards 13, 14. As the position of the center of gravity of the mattress on its own is known, the center of gravity of a patient on the mattress can then be determined and used as part of a patient position monitoring system or apparatus.

The bed control box includes a buzzer 17 or alarm for warning a care giver if the patient position indicates a dangerous or potentially dangerous position, or bed exit is imminent or has happened. Bed exit is imminent when the center of gravity moves towards the edge of the bed. A center of gravity moving or moved towards the edge of the bed also indicates a potentially dangerous position with a possible fall from the bed being imminent or more likely. The bed control box also controls the actuators which control the height and orientation of the support deck and has a control pad for doing that. The control panel may be fixed to the side of the bed or be remote from the bed and the remaining elements of the bed control box may be located on the bed frame or underneath the support deck.

Figure 6:
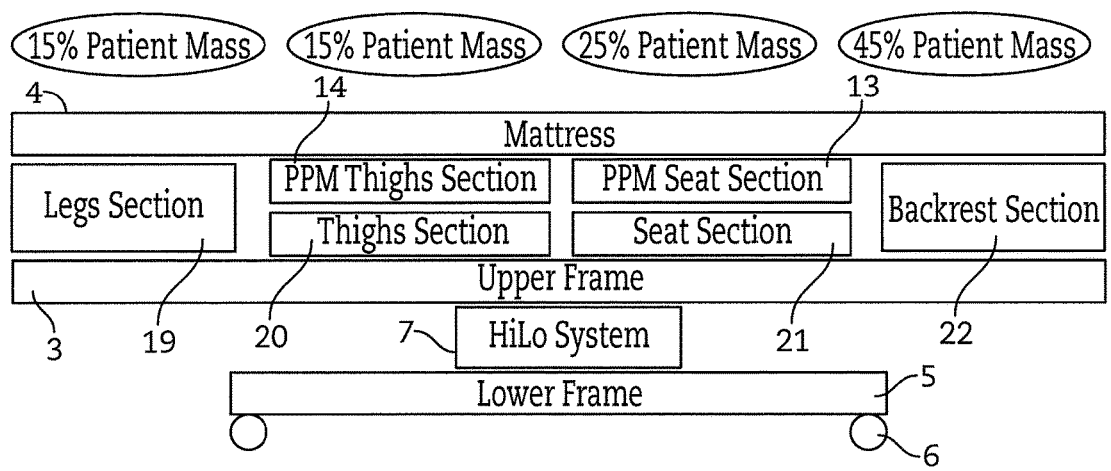
FIG. 6 is a cross-sectional schematic view corresponding to the bed of FIGS. 1 and 2.

Referring to FIG. 6, the mattress support deck 2 is divided into a deck by section 19, deck thigh section 20, deck seat section 21 and deck back rest section 22. These sections may be arranged so as to take up different configurations with, for example, the back rest section 21 fitted so as to provide support to a patient sitting up on the bed. The thigh sensing board 14 is located on the deck thigh section 20 and the seat sensing board 13 is located on the deck seat section 21.

When a patient is lying flat on the bed in a normal position, the typical maximum proportion of the patient load or weight on the different sections is, 15%, 15%, 25% and 45% of the patient mass for, respectively, the deck leg section 19, deck thigh section 20, deck seat section 21 and deck back rest section 22. The center of gravity of the entire patient can therefore be determined from the loads on the load cells 9 of the thigh 14 and seat 13 sensing boards.

The embodiment of FIGS. 2 to 4 has a pair of substantially rigid sensing boards 13, 14 each having four load cells 9 each located at one of the four corners of the substantially rectangular sensing boards. The sensing boards may, if necessary, be retro-fitted to existing beds by taking the place of existing support elements and/or be laid on top of the existing upper frame.

Figure 7:
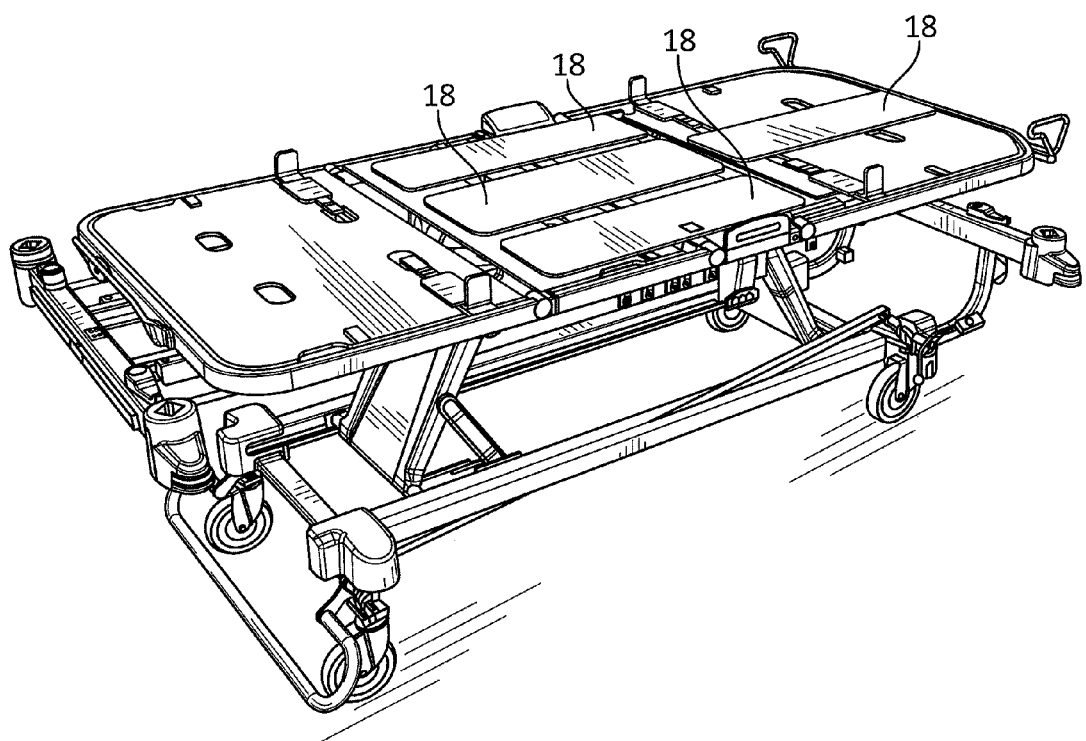
FIG. 7 is a top perspective view of an alternative embodiment showing a bed (hospital or long term care) with the mattress removed.
Figure 8:
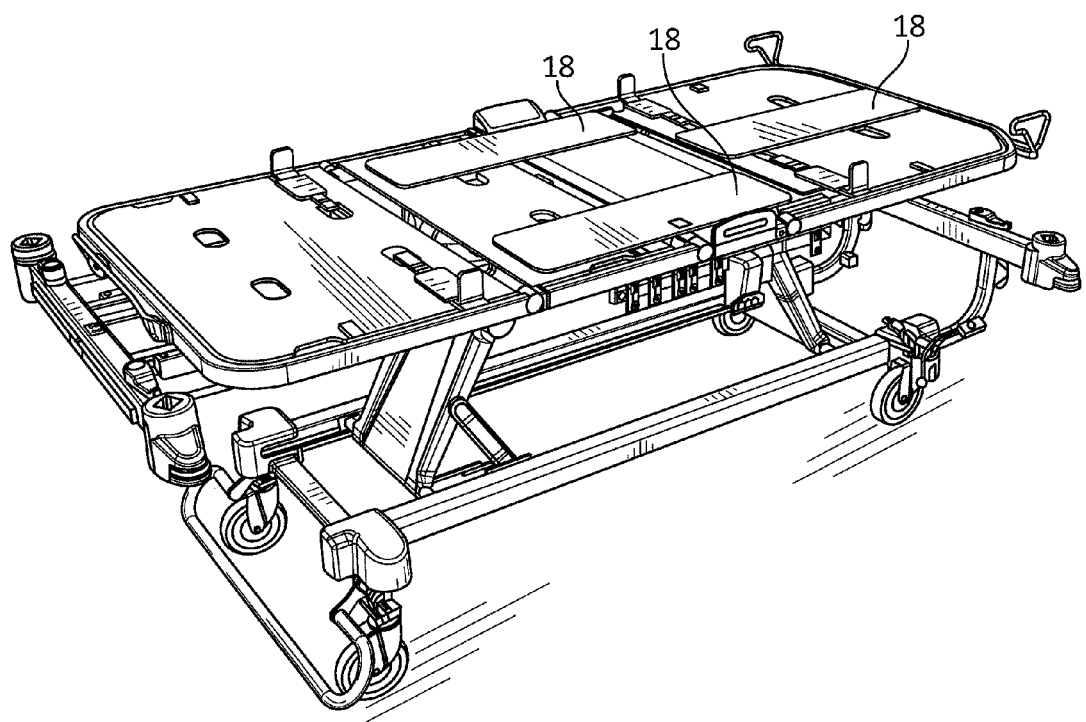
FIG. 8 is a top perspective view similar to that of FIG. 7 and showing an alternative sensing cell configuration.

The alternative embodiments illustrated in FIGS. 7 and 8 include thin flexible sensing pads 18 located on and fixed to the upper surface of the support deck 2. The thin flexible sensing pads 18 may be capacitive or dielectric sensors. The flexible sensing pads 18 may be located to the seat and thigh sensors (not shown). In an alternative embodiment (not shown in the Figs.) the capacitive or dielectric sensing elements may be attached to or integral with the lower surface of the mattress 4.

The functionality of the patient position monitoring hardware 10 and software 11 will now be described in relation to an embodiment that uses two detection boards of the sort shown in FIGS. 4 and 5. In combination, the hardware 10 and software 11 will be referred to as a monitoring system, which in conjunction with the sensors allows the position of a patient on the support apparatus to be monitored and causes an alarm to be activated if the system determines that the patient has shifted their weight beyond that permitted by predetermined parameters.

The system functions by monitoring variables determined based upon output from the sensors. Optionally, these variables may include a patient gravity center position and patient weight. One or more detection modes can be defined and implemented using the system based upon user selection, each detection mode having different predetermined parameters. These detection modes may include: a high sensitivity mode to monitor and alert for relatively small movements of a patient, applicable to patients who have tubes in their mouths or throats for example; a medium sensitivity mode used to monitor mobile patients and alert a caregiver if the patient attempts to sit up, or roll towards a side of the bed; and a low sensitivity bed exit mode used to monitor mobile patients to ensure they remain "in bed".

As an example, the following sensors and values may be used. SS1 to SS4 refer to the sensors on the seat board, with SS1 corresponding to the left hand side nearest to the head side of the board, SS2 corresponding to the left hand side nearest to the feet side of the board, SS3 corresponding to the right hand side nearest to the feet side of the board and SS4 corresponding to the right hand side nearest to the head side of the board. ST1 to ST4 refer to corresponding sensors, in corresponding respective positions, on the thigh board. SSR and SSL refer to the sum of the values of the right hand side seat sensors ($\Sigma$ SS3 SS4) and left hand side seat sensors ($\Sigma$ SS1 SS2) respectively. STR and STL refer to the sum of the values of the right hand side thigh seat sensors ($\Sigma$ ST3 ST4) and left hand side seat sensors ($\Sigma$ ST1 ST2) respectively. The global weight, Gw, is the sum of the values for the various sensors, and in this example is the sum of the left and right hand values for both boards (SSL+SSR+STL+STR). The center of gravity, Gc, may be calculated in any appropriate manner, and for example as a function of the sum of the values of the sensors, the global weight and the width of the respective sensor boards, or the lateral separation between the left and right hand sensors on the boards. For example, Gc may be calculated as follows:

$$Gc = \frac{\left[(SSL-SSR)\left(\frac{Wsb}{2}\right) + (STL-STR)\left(\frac{Wtb}{2}\right)\right]}{Gw}$$

Where Wsb and Wtb are respectively the width of the seat and thigh boards, or the lateral separation between the left and right hand sensors on the boards.

In order to initiate patient monitoring the system may optionally require a calibration to be carried out. The output values of the sensors are determined for both boards with only the patient support element (e.g. a mattress) in position. This provides the initial "zero" values for the sensors without the patient, which may be stored in a memory accessible by the hardware 10. The patient is then positioned on the patient support element in a centered position, appropriately aligned.

In order to correctly position the patient, the monitoring system may optionally rely upon correct positioning by the caregiver, for example by aligning the patient using markings provided on the patient support element. As an example, markings may be provided to align the patient's hips in the desired position. Alternatively, or in addition, the monitoring system may be configured to analyze the sensor outputs to determine whether the patient is in the correct position, within a predetermined tolerance, for the system to start monitoring patient positioning.

In particular, the monitoring system may be configured to compare the right hand side sensor values (SSR, STR) and left hand side sensor values (SSL, STL) for a given board to determine whether the patient is adequately aligned. This may involve determining an initial value for the center of gravity, Gc, and ensuring that it is within a predetermined tolerance range, such as within 100 mm of the center of the support apparatus measured along its width. The system may include a visual and/or audio output indicative of whether the patient is correctly positioned within the predetermined tolerance range. For example, one or more LEDs may indicate by steady illumination that the patient is correctly positioned and may blink or flash to indicate that the patient is not correctly positioned. A failure indication requires the caregiver to reposition the patient correctly, or may be indicative of other faults such as a system overload, sensor shock or sensor deterioration.

In addition to applying an initiation tolerance for the position of the center of gravity, the monitoring system may be further configured to apply a minimum weight requirement, whereby the total weight Gw must exceed a particular value for the system to activate. Tests have found that center of gravity calculations can become unstable if a minimum weight requirement is not applied. The minimum weight may be determined by experiment, for example by comparing global patient weights as detected by the sensors with the actual patient weights. The minimum weight is compared against the total weight detected by the seat and thigh sections to determine if the minimum weight requirement is met. An example minimum weight could be 6 kg.

Once the patient has been correctly positioned, and the minimum weight requirement is met, initial sensor values are saved. The individual values themselves may be saved, or combined initial values SSLinit, SSRinit, STLinit and STRinit may be saved. In addition, initial values Gw_init and Gc_init for Gw and Gc may be saved as well as a value BA_init for the initial backrest angle as will be described below.

The monitoring system is then ready to receive input indicative of the detection sensitivity level desired for the patient. The monitoring system functions by periodically determining whether the sensor outputs indicate the patient has moved from a desired position. The determination can be made based upon a change in center of gravity, Gc, a change in global weight Gw, or a combination of the two.

A value for the center of gravity, Gc, for a patient can be calculated as above, or in any suitable manner, based on the sensor outputs. The monitoring system determines whether the value for Gc falls within a predetermined range of values. In the present embodiment Gc may be calculated only in a single dimension, laterally along the width of the support apparatus locating the position of Ge between the sensors. In other embodiments Gc could be calculated in two dimensions, with a range applying to the position of Gc within each of the desired dimensions. For example, the position of the center of gravity along the length of the support apparatus may also be determined, and threshold parameters applied thereto in the same manner as described for the width of the apparatus.

In addition, or as an alternative, to using Gc the system may use a shift in total weight Gw as a parameter for determining whether a patient has moved from a desired position. Variation in both Gc and Gw parameters may be determined relative to the initial values determined during initial patient placement, or could be compared to a predetermined reference value.

A plurality of different preset detection levels are provided, depending upon the patient condition. The presets use different permissible value ranges for Gc and/or Gw to provide different sensitivities to patient movement. Examples of different detection levels are provided below.

A first detection level may be limited to a patient moving a relatively small amount within a predefined area A of the patient support apparatus. This detection level can be used when the caregiver wishes to be alerted when the patient begins to move.

A lateral movement of Gc along the width of the patient support apparatus may be permitted within a relatively small tolerance, VL1_DX, for example ±50 mm, before an alarm is activated. In particular, the alarm may be activated if Gc−Gc_init falls outside ±VL1_DX. In this way, an alarm is initiated when the patient moves towards either side of the patient support apparatus.

In addition, the first detection level may also activate an alarm if the patient load Gw varies by a predetermined amount VL1_LV from the initial value, such as a 15% variation. For each state change of the system (new values of sensor signals), the algorithm analyzes the minimum and maximum values to calculate the load variation. If the variation is greater than 15% the alarm is triggered. A variation of Gw, as detected by the sensor boards, indicates a longitudinal displacement of the patient's weight along the bed. In this way, an alarm is initiated when the patient moves away from the head section such as by sitting up in bed.

A second detection level may permit the patient to move by an amount greater than the first detection level, allowing the patient to move within an area B, larger than area A, before an alarm is activated.

According to the second detection level the lateral movement of Gc may be permitted within a larger tolerance, VL2_DX, for example ±250 mm. In particular, the alarm may be activated if Gc−Gc_init falls outside ±VL2_DX.

In addition, the second detection level may also activate an alarm if the total patient load Gw varies by a predetermined amount from the initial value, such as a 50% variation. In particular, the variation may be a decrease in the total patient load. This defines a trigger limit when the patient moves in the longitudinal direction of the bed towards the head or the foot, as weight shifts from the seat and thigh board sections when the patient repositions.

In this way, according to the second detection level, an alarm is activated when the patient center of gravity moves outside an area B, bigger than area A, and/or more than a predetermined amount of the patient weight shifts from the support apparatus. The alarm activates when the patient moves away from the center of the bed towards an egress point and can be used when a caregiver wishes to be alerted of an attempted egress by the patient.

A third detection level may trigger the alarm when the variation in Gw is over a given threshold such that the alarm activates when the patient's weight shifts significantly off the frame of the bed. This mode can be used when a caregiver wishes the patient to move freely within the bed, but to be alerted when the patient leaves the bed.

In order to provide an alarm before the patient exits the bed, the system needs to detect the load variation and a percentage of weight discharged from the bed. Therefore, for the third detection level, the system may trigger the alarm when a predetermined proportion, such as 70%, of the patient's load moves out of the bed. The third detection level may therefore allow a weight shift greater than the second detection level before activating the alarm.

An alarm delay functionality may optionally be provided in conjunction with one or more of the detection levels. This allows the patient to reposition without the alarm activating provided that they do so within a predetermined amount of time. Delays may be included to improve overall system stability and to prevent false alarms occurring.

As an example, with the third detection level it may be desirable for the patient to be able to get up and leave the bed for a predetermined period of time before the alarm is activated. If the patient returns to a position within the tolerances for the particular level then supervision by the system resumes without the alarm being activated. The delay, in this case, may be a number of minutes, such as 30 minutes.

A relatively short delay may be desirable in some embodiments, on the order of a few seconds, to prevent small shifts in patient position setting off the alarm. The delay may be between 0.5 and 5 seconds, and may be around 1.5 seconds, for example. Such delays may be particularly desirable in conjunction with detection levels of the second and third type, where the patient is expected to have some degree of mobility.

The delay may be user selectable, for example at the time of choosing the detection level being applied to the patient.

The delay may also, or alternatively, be dependent upon the positioning of Gc, such that the delay is only applied when the variation in Gc is within a predetermined limit. As an example, the delay may be applied to the third detection level when Gc varies by 250 mm. If Gc varies by more than this amount then the alarm may not be delayed, such that the alarm is more reactive. This accommodates for patients shifting their weight, and assumes that a patient whose weight is positioned near to the edge of the bed is more likely to be trying to exit the bed such that a change in global weight requires immediate alert to the care giver.

In order to determine whether an alarm is to be activated the system processor analyses all the signals provided by or to the system, including detection signals (DS) from the sensors and selection signals from a user input device such as a control panel. The selection signals include a selected detection level (SL) and may also include a selected delay (SD). The analysis compares the signals with stored rules and triggers the alarm depending upon whether the rules are met. If the level detected is the same after all sensors refresh then the system is stable.

Optionally the values of the center of gravity, Gc, and/or the global weight, Gw, may be subject to corrections to account for one or more of the angle of a back rest and the type of patient support element used.

For embodiments in which the patient support apparatus includes an adjustable back rest, the back rest can move from between a first angle and a second angle, such as from a substantially flat position to an angle that supports a patient in a sitting position. The angle of the back rest can affect the distribution of the patient's weight on each of the sensor boards.

When the back rest is raised or lowered, the gravity center Gc is modified by the mattress mass supported by the backrest frame. To correct for this error a rule is applied to modify the center of gravity as a function of the angle of the backrest. The modified center of gravity may be calculated based on the backrest angle (BA) and the mattress weight (Mw), taking into account the detected weight of the patient. In particular, the backrest angle compensation to Gc may be calculated as: $Gc\_c=Gc*Gw/(Gw-Mw*\sin^2(BA))$.

A correction to the value of the weight Gw can also be made, factoring in the back rest angle. In particular, a corrected value Gw_ref may be determined as a function of Gw_init and the change in backrest angle. To correct the load applied on the sensors when the backrest moves the corrected weight Gw_ref may be calculated as: $Gw\_ref=Gw\_init*law(BA)/law(BA\_init)$. Gw_init is the initial weight detected using the sensors when the system is activated, BA is the measured backrest angle, and BA_init is the initial backrest angle. The function "law(X)" is a predetermined function determined by experiment, with one example being: $law(X)=(a*x^3+b*x^2+C*x+d)/d$. The coefficients a, b, c and d are determined by experiment and may vary depending upon the type of mattress used.

The angle of the back rest may be determined continuously or at regular intervals using an accelerometer. It is possible to use a different type of device to detect the backrest position provided the device signal can be translated into an angle to allow the correction law to be applied. Other embodiments may allow the user to input a value indicative of the angle of the back rest, if this value is fixed whilst the patient is in the bed.

It has been appreciated that the type of patient support element may affect the distribution of weight of the patient and therefore may affect the calculated center of gravity. Therefore, the calculation of Gc, or alternatively the rule threshold values for Gc, may be corrected to account for the type of mattress. For example, the value of Gc may have a correction factor applied depending upon the type of mattress. In particular, the correction factor may differ depending upon whether the mattress is a foam or air variety.

It has been appreciated that for certain lateral positions foam mattresses tend to result in an absolute value for Gc that is too large (i.e. further from the center of the bed than it should be) and that air mattresses tend to result in an absolute value for Gc that is too small (i.e. closer to the center of the bed than it should be). Since different detection levels may rely upon different threshold values for Gc the correction applied based on mattress type may vary depending on the selected detection level. The caregiver may provide a selection indicative of the mattress type to the system at the initiation/calibration stage.

Figure 9:
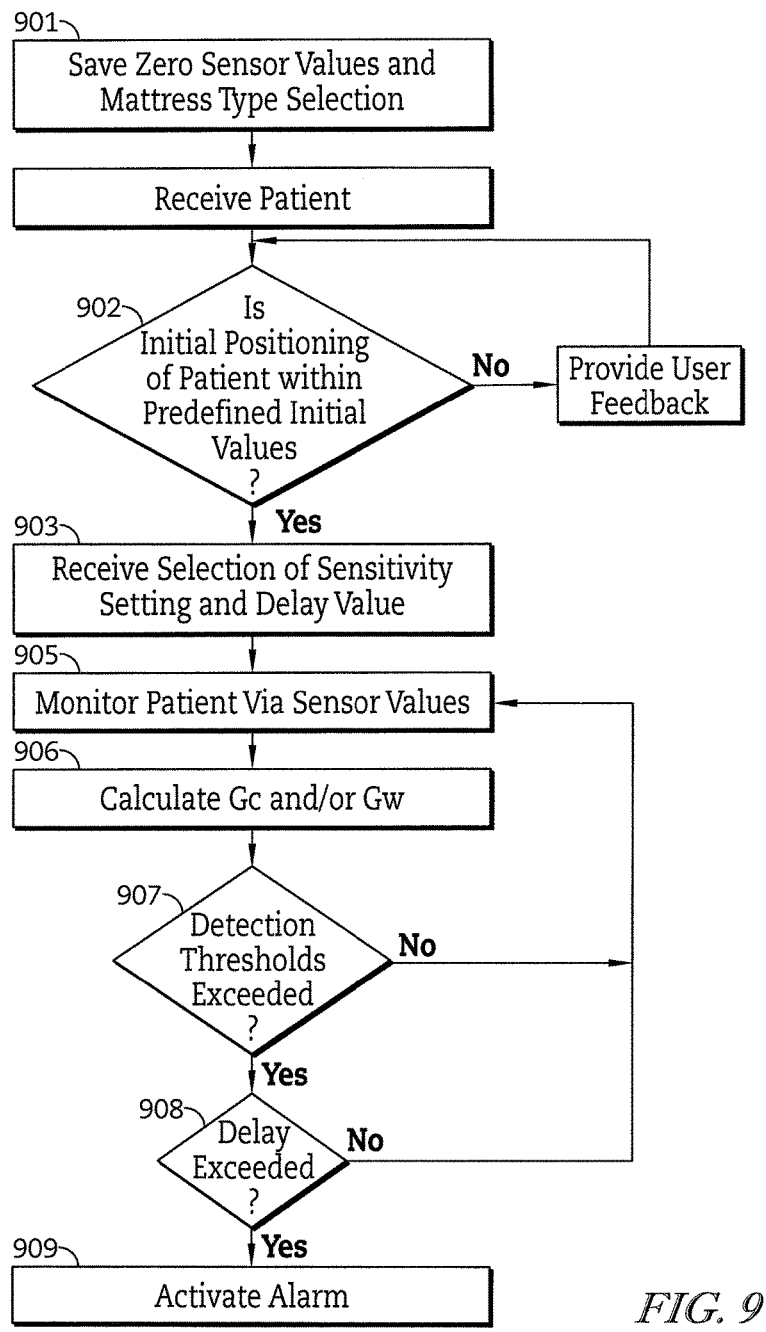
FIG. 9 is a diagram showing a method for setting detection parameters and detecting patient movement.
Figure 10:
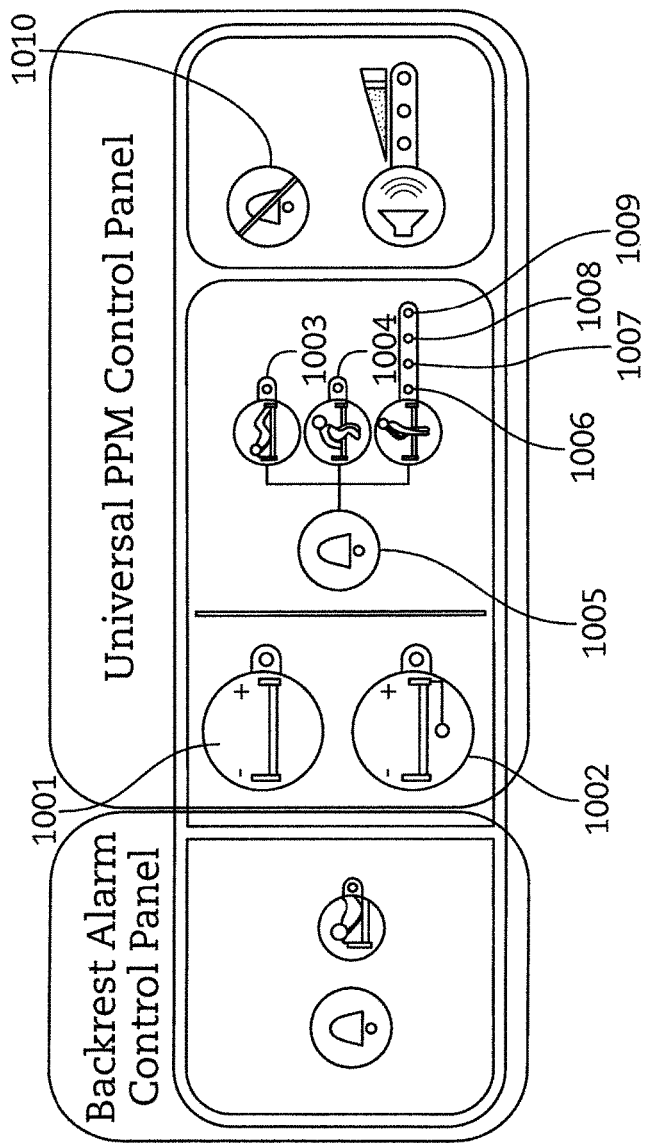
FIG. 10 is a front view of a user interface for setting detection parameters.

A method for using the monitoring system will now be described with reference to FIGS. 9 and 10. Initially the caregiver sets the system to its zero setting by selecting the appropriate option 1001 or 1002 on the interface panel. In this example the zero selection also optionally selects the type of mattress being used, which affects subsequent calculations as mentioned above. Button 1001 selects a foam mattress and zeros the system, whereas button 1002 selects an air mattress and zeros the system. At step 901 the monitoring system saves the zero sensor values, being the sensor values for the mattress without the patient, as well as the optional mattress type selection. The patient is then placed on the mattress and the positioning and minimum weight step 902 is carried out, whereby the patient is correctly positioned based upon feedback from the monitoring system. If the patient is correctly positioned then the interface will indicate this to the user by lighting up the level LEDs 1003, 1004 and 1005, or by providing some other form of visual or audible indication. If the patient is incorrectly positioned the level lights may blink and/or an audible indication such as a buzzer may be given prompting the caregiver to reposition the patient until the desired initial positioning is achieved.

Once the patient has been placed in the correct initial position the method moves on to a selection of the desired sensitivity level of the monitoring system. At step 903 the user selects the desired detection level by pressing the button 1005, the selection being indicated by LEDs 1003, 1004, 1006, 1007, 1008 or 1009 on the interface. In this example, three possibilities, SL1, SL2 and SL3 are provided, corresponding to levels 1, 2 and 3 described above. For certain detection levels, in this example SL3, there may also be an option at step 903 to select a desired delay value which will prevent the alarm from activating until the detected patient properties are outside the predetermined ranges of the particular detection level for the predetermined delay value. In this example LEDs 1006 to 1009 indicate respectively whether a delay of 0, 5, 10 or 15 minutes has been selected, although other delays are possible.

The monitoring system then begins monitoring the patient, the LED lights being illuminated to indicate the selected detection level. The alarm will now activate according to the detection thresholds defined in the variable parameters associated with the selected detection level. The initial sensor values may be saved at this point, or they may be saved earlier when the initial patient positioning has been completed.

The monitoring system periodically obtains the sensor values at step 905. The corrections required due to back rest angle and mattress type may also be optionally applied before the sensor values are used to calculate current values for Gc and Gw at step 906, which can be compared against the initial values, at step 907, to determine whether the patient parameters have moved outside the predetermined ranges specified by the selected detection level. The system repeatedly checks the patient parameters based upon the sensor values in accordance with the selected detection level.

Alarm activation 909 is determined in accordance with whether the patient parameters have fallen outside the predetermined ranges associated with the selected detection level. Alarm activation may factor in whether a delay 908 has been included. A mute button 1010 may be provided to deactivate the alarm manually.

Whilst the functionality of the patient position monitoring unit 2 has been described in relation to a patient support apparatus having two sensor boards each with four sensors it will be appreciated that more or fewer sensors can be used. Embodiments may, for example, use two sensors, laterally displaced from one another, such that a center of gravity along at least one dimension of the patient support apparatus, and optionally an overall indication of weight, can be determined.

The functionality of the patient position monitoring hardware 10 and software 11 has been described in relation to an embodiment of the sort shown in FIGS. 4 and 5. It will be appreciated that this functionality could be employed in any of the embodiments of the patient support apparatus or sensing boards as described herein. It is also possible to apply this functionality to any patient support apparatus having sensing elements for measuring the weight of a patient and mattress, whether the sensors are located on the patient support deck, or elsewhere such as under the mattress supporting portion of the bed.

The systems and arrangements described above can be used to detect movement by noting changes in the location of the center of gravity. They can therefore also be used to detect inactivity. In such a capacity they could form part of a system or care protocol to, for example, reduce the risk of pressure ulcers, bed sores and other ailments which are or can be associated with prolonged periods of inactivity or bed rest.

Hospitals have specific procedures to reduce the risk of pressure ulcers and other ailments which are associated with prolonged periods of inactivity. These include repositioning of the patient at defined intervals and/or the use of inflatable air mattresses such as those described in, for example, EP 2198822. However, it is not always easily and/or immediately recognized when a particular patient is at risk of developing bed sores, pressure ulcers and/or similar, and should therefore be placed on a bed with an air mattress of the type developed and available for reducing the risk of such ailments. Patients are often placed on simple non-inflatable foam or similar mattresses at the start of their hospital stay. The systems described above are particularly suitable for use with such a foam or standard mattress to detect prolonged inactivity and hence a risk of pressure ulcers, bed sores and/or the like. A system could be provided in which the arrangements for detecting the center of gravity and hence the movement of the center of gravity associated with movement of the patient above could be used to detect inactivity on a standard or foam mattress. When a defined prolonged period of inactivity is sensed or determined an alarm could be activated and/or a message displayed on a care giver screen prompting the care giver to alter the change to the standard mattress for an air mattress (or similar) designed to reduce the risk of bed sores etc, or reposition the patient.

Although certain illustrative embodiments have been described in detail above, variations and modifications exist within the scope and spirit of this disclosure as described and as defined in the following claims.

The invention claimed is:
1. A patient support apparatus comprising
a main frame,
an articulated mattress support deck supported on the main frame, the articulated mattress support deck comprising a seat section, a head section that articulates relative to a head end of the seat section, a thigh section that articulates relative to a foot end of the seat section, and a leg section that articulates relative to the thigh section, wherein at least one of the seat section and the thigh section includes a section frame, a mattress support panel, and a plurality of load sensors supporting the panel above the section frame, the plurality of load sensors providing signals indicative of a portion of a patient's weight, one or more processors coupled to the plurality of load sensors, and a mattress supported on the articulated mattress support deck, wherein the one or more processors are configured to process signals from the plurality of load sensors differently depending upon whether an input to the one or more processors indicates that the mattress is a foam mattress or an air mattress.

2. The patient support apparatus of claim 1, wherein each of the seat section and the thigh section includes a respective section frame, a respective mattress support panel, and a plurality of load sensors supporting each panel above the respective section frame.

3. The patient support apparatus of claim 2, wherein the respective mattress support panels are each generally rectangular in shape and wherein each load sensor of the plurality of load sensors is located beneath a respective corner region of the respective mattress support panel.

4. The patient support apparatus of claim 2, wherein the head section and the leg section are devoid of any load sensors.

5. The patient support apparatus of claim 2, wherein each load sensor of the plurality of load sensors is attached to an underside of the respective mattress support panel.

6. The patient support apparatus of claim 1, wherein the mattress support panel is generally rectangular in shape and wherein each load sensor of the plurality of load sensors is located beneath a respective corner region of the mattress support panel.

7. The patient support apparatus of claim 1, wherein the head section and the leg section are devoid of any load sensors.

8. The patient support apparatus of claim 1, wherein each load sensor of the plurality of load sensors is attached to an underside of the mattress support panel.

9. The patient support apparatus of claim 1, wherein each load sensor of the plurality of load sensors comprises a strain gauge sensor.

10. The patient support apparatus of claim 1, wherein the one or more processors are configured to determine a location of the center of gravity of a patient on the patient support element, along a width of the patient support apparatus, based upon outputs from the plurality of load sensors.

11. The patient support apparatus of claim 10, wherein the one or more processors are further configured to determine a load variation, being a variation in total force applied to the plurality of load sensors.

12. The patient support apparatus of claim 11, wherein the one or more processors are further configured to receive at least one user input selecting one of two or more presets, each preset corresponding to a patient movement sensitivity level and comprising a predetermined range of values for the location of the center of gravity and/or a predetermined load variation value.

13. The patient support apparatus of claim 12, wherein the one or more processors are further configured to provide an output to activate an alarm in response to the location of the center of gravity along the width of the patient support apparatus being outside the predetermined range of values and/or the load variation exceeds the predetermined value.

14. The patient support apparatus of claim 12, further comprising an angle sensor to sense an angle of inclination of the head section, and wherein the one or more processors are further configured to receive an input indicative of the angle of the back rest and to adjust the predetermined range of values for the location of the center of gravity and/or the predetermined load variation value as a function of the angle of the head section.

15. The patient support apparatus of claim 14, wherein the angle sensor comprises an accelerometer.

16. The patient support apparatus of claim 1, wherein the section frame includes a pair of spaced apart frame members, each frame member supporting at least one load sensor of the plurality of load sensors.

17. The patient support apparatus of claim 16, wherein a first frame member of the pair of frame members supports first and second load sensors of the plurality of load sensors and wherein a second frame member of the pair of frame members supports third and fourth load sensors of the plurality of load sensors.

18. The patient support apparatus of claim 16, wherein each frame member of the pair of frame members extends generally parallel with a width of the patient support apparatus.

19. A patient support apparatus comprising a main frame, an articulated mattress support deck supported on the main frame, the articulated mattress support deck comprising a seat section, a head section that articulates relative to a head end of the seat section, a thigh section that articulates relative to a foot end of the seat section, and a leg section that articulates relative to the thigh section, wherein at least one of the seat section and the thigh section includes a section frame, a mattress support panel, and a plurality of load sensors supporting the panel above the section frame, the plurality of load sensors providing signals indicative of a portion of a patient's weight, one or more processors, coupled to the plurality of load sensors, the one or more processors being configured to determine a location of the center of gravity of a patient on the patient support element, along a width of the patient support apparatus, based upon outputs from the plurality of load sensors, wherein the one or more processors are further configured to determine a load variation, being a variation in total force applied to the plurality of load sensors, wherein the one or more processors are further configured to receive at least one user input selecting one of two or more presets, each preset corresponding to a patient movement sensitivity level and comprising a predetermined range of values for the location of the center of gravity and/or a predetermined load variation value, and a mattress supported on the articulated mattress support deck, wherein the at least one user input received by the one or more processors indicates whether the mattress is a foam mattress or an air mattress.

20. The patient support apparatus of claim 19, wherein the one or more processors are further configured to adjust the predetermined range of values for the location of the center of gravity and/or the predetermined load variation value based on whether the mattress is the foam mattress or the air mattress.

* * * * *